United States Patent [19]

Borsa et al.

[11] Patent Number: 4,699,911

[45] Date of Patent: Oct. 13, 1987

[54] LEVO AND DEXTRO DROPROPIZINE HAVING ANTITUSSIVE ACTIVITY

[75] Inventors: Massimiliano Borsa; Giancarlo Tonon; Salvatore Malandrino, all of Milan, Italy

[73] Assignee: Dompe' Farmaceutici S.p.A., Milan, Italy

[21] Appl. No.: 906,698

[22] Filed: Sep. 11, 1986

Related U.S. Application Data

[63] Continuation of Ser. No. 686,709, Dec. 27, 1984, abandoned.

[30] Foreign Application Priority Data

Dec. 29, 1983 [IT] Italy ................................ 24430 A/83

[51] Int. Cl.$^4$ ................... A61K 31/495; C07D 241/00
[52] U.S. Cl. ...................................... 514/255; 544/392
[58] Field of Search .......................... 544/394; 514/255

[56] References Cited

U.S. PATENT DOCUMENTS 3,163,649 12/1964 Morren ............................... 544/394
4,372,958 2/1983 Pestellini et al. .................. 544/394

FOREIGN PATENT DOCUMENTS 601394 3/1961 Belgium .
1534651 6/1968 France ............................... 544/394

OTHER PUBLICATIONS

Morren, Chem. Abst. 56–2460d, eq. Belg. 601394.
Burger, Medicinal Chemistry Part II, 1980, Chapter Fifty-three, pp. 759–785.

*Primary Examiner*—Donald G. Daus
*Assistant Examiner*—Cecilia Shen
*Attorney, Agent, or Firm*—Walter H. Schneider

[57] ABSTRACT

The optical isomers of 3-(4-phenyl-1-piperazinyl)-1,2-propanediol, a process for the stereo-selective preparation and pharmaceutical composition containing the same as active principles are described.

2 Claims, No Drawings

LEVO AND DEXTRO DROPROPIZINE HAVING ANTITUSSIVE ACTIVITY

This is a continuation of application Ser. No. 686,709 filed Dec. 27, 1984, now abandoned.

The present invention refers to the optical isomers of 3-(4-phenyl-1-piperazinyl)-1,2-propanediol having formula (I)

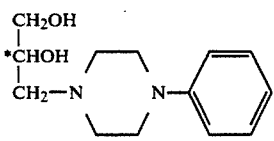

The compound I, because of the presence of the asymmetric carbon atom marked by the asterisk, exists as a couple of dextrorotatory and laevorotatory isomers, never described before and which are the object of the present invention due to their completely surprising properties.

The compound I, also known with the name of dropropizine, is an antitussive agent used for a long time in human therapy in form of racemic mixture (Belgian Pat. No. 601,394). It has now been surprisingly found, and it is the object of the present invention, that the two separated isomers possess distinct pharmaco-therapeutic features which are particularly advantageous in comparison with the racemic mixture. Namely, the laevorotatory isomer has shown the same antitussive activity as the racemic mixture but having a remarkably lower activity degree on the central nervous system. In other words, the activity of the laevorotatory isomer is much more selective, with lower undesired side-effects.

These differences are completely unexpected and unforeseeable for antitussive drugs of the non narcotic type. In fact, differently from other classes of compounds whose isomers notoriously show qualitative and/or quantitative differences in pharmacological activity, such as in the instance of arylpropionic antiinflammatory agents (naproxen, benoxaprofen, carprofen) (J. Pharm. Pharmacol. 35, 693–704, 1983), beta adrenergic receptor blocking agents (salbutamol, propranolol) (Burger Medicinal Chemistry, 4th Ed., part III, Wolff. J. Wiley N. 5, pag.225–283, 1981), and opioid drugs (morphine, codeine, narcotine, propoxyphene and the like) (J. Pharmacol. Exptl. Therap., 226, 108–113, 1983), for antitussive non narcotic drugs such as dropropizine, zipeprole, eprazinone and oxolamine such differences in activity of the isomers have never been reported.

The improvement in the activity/side effect (action on CNS) ratio obtained by means of the dropropizine isomers involves a remarkable therapeutic advantage, being all the known antitussive agents endowed with centrale sedative action (D. Miller, Antitussive-Burger Med. Chem., 4th Ed., part III, Ed. Wolff, J. Wiley N.Y., pag. 759–785, 1981).

The compounds according to the present invention can be obtained starting from racemic dropropizine by conventional optical resolution methods, or they can be synthesized starting from optically active 1,2-isopropylidene-sn-glycerol according to a process which is a further object of the invention.

According to the process of the invention the laevorotatory isomer is prepared, for instance, starting from (+)-1,2-isopropylidene-sn-glycerol which is, after transformation into the corresponding tosylate, subjected to deketalization, yielding the (−)-glycerol-1-tosylate: the condensation with N-phenylpiperazine finally yields the laevorotatory isomer of I. The dextrorotatory isomer is on the contrary obtained starting from (+)-glycerol-1-tosylate.

The preparation of the optically active isopropylidene-sn-glycerols necessary for the process according to the invention can be carried out in two ways: the first (Method A), used for the (−)isomer, concerns the conversion with nitrous acid of L-serine to L-glyceric acid, the esterification of the latter with methanol into 2,2-dimethoxypropane and subsequent ketalization with acetone.

The ketalization can be carried out in 2,2-dimethoxypropane in the presence of acids such as p-toluensolphonic acid or, alternatively, in the presence of Lewis acids such as zinc chloride, using acetone as the solvent.

The (−)-methyl- or -isopropylidene-L-glycerate so obtained is then reduced to glycerol by means of metal hydrides such as lithium aluminium hydride, or by means of other suitable reducing agents. The employed method, slightly modified, is reported by C. H. Lok, J. P. Ward; D. A. Van Dorp, Chem. and Physics of Lipids 16, 115 (1976).

The second preparation method (Method B) of the dextrorotatory isomer of isopropylidene glycerol, comprises the ketalization of D-mannitole with acetone in the presence of zinc chloride, the cleavage with periodates and the subsequent reduction with alkaline hydrides. The employed process, slightly modified, is reported by H. Eibl., Chem. and Physics of Lipids 28, 1 (1981).

The isomers object of the invention can be formulated in pharmaceutical compositions suited for the oral administration, in combination with excipients conventionally used in pharmaceutical preparation. Liquid oral compositions such as syrups, solutions, drops, elixirs, etc., are particularly suited for the designated therapeutic use. The compositions according to the invention contain from 10 to 100 mg of active principle and can be administered three or more times a day, depending on the severity of symptomathology, and weight and age of the patient.

Screening for anti-inflammatory activity has been carried out employing the established carrageenin and ovoalbumin oedema tests in the rat, according to the methods described by C. A. Winter et al., Proc. Soc. Exp. Biol. Med., 111, 544, 1962 and Turne in "Screening Methods in Pharmacology" Acad. Press N.Y., cpt. 14, p. 164, 1965, respectively. The results are reported in Table I.

The compounds under exam have been administered by the oral route one hour before the injection of the phlogistic agent.

TABLE I

Antiinflammatory activity of (±) racemic dropropizine, (+) destrorotatory isomer and (−) laevorotatory isomer, at different times from the phlogosis induction.

| | \multicolumn{6}{c}{$DE_{50}$ mg/kg p.o. (C.L. 95%)} | | | | | |
|---|---|---|---|---|---|---|
| | Oedema by carrageenin | | | Oedema by ovoalbumin | | |
| | 1st hour | 3th hour | 6th hour | 1st hour | 3th hour | 6th hour |
| (±) | 39.0 (33.7–44.9) | 77.9 (57.6–105.5) | 117.3 (83.1–141.4) | 23.6 (20.5–22.1) | 28.5 (25.1–32.4) | 37.1 (29.8–46.2) |
| (+) | 43.9 (30.8–62.7) | 80.5 (52.4–94.9) | 69.7 (42.3–114.9) | — | — | — |
| (−) | 232.9 (193.9–279.7) | 212.5 (179.8–251.4) | 240.8 (191.7–289.7) | 55.6 (46.5–66.5) | 72.2 (59.7–87.4) | 121.4 (81.8–180.2) |

C.L. = Confidence limits.

The results of the antitussive activity tests, carried out in the guinea pig after electrical stimulation of the vagus nerve and exposure for 5 minutes to a 5% citric acid aerosol according to the methods of R. M. Piekirning et al., Arzn. Forsch., 29, 287, 1979 are reported in Table 2.

The compounds under exam have been administered intravenously 5 minutes before the electric stimulation and orally 60 minutes before the citric acid aerosol.

TABLE 2

Antitussive effect of (±) racemic dropropizine, (+) dextrorotatory isomer, (−) laevorotatory isomer and codeine.

| | $DE_{50}$ mg/kg (C.F. 95%) | |
|---|---|---|
| | Electric stimulus | 5% Citric acid |
| (±) | 11.73 (9.14–14.41) | 117.11 (98.35–139.48) |
| (+) | 23.52 (11.88–46.58) | 140.80 (119.04–166.65) |
| (−) | 13.51 (10.3–17.71) | 150.85 (126.32–180.15) |
| Codeine | — | 65.07 (57.02–74.23) |

C.F. = Confidence limits.

Tests have been carried out to determine the CNS activity, by evaluating the influence on the sleeping time induced by barbiturates in the mouse, according to the method of F. M. Berger "Methods in Drug Evaluation" Proc. Int. Symp. Milan, Sept. 1965, North Holland Pubbl. Co., and by recording the electroencephalographic and electromiographic curves in the rat with chronically implanted electrodes, calculating the time (in seconds) in the awakening and sleeping condition (including synchronized and unsynchronized sleep). The results are reported in Table 3.

The compounds under exam have been administered orally, in the sleeping time test 30 minutes before the i.p. injection of 35 mg/kg of secobarbital, while in the electroencephalographic test at the beginning of recording.

TABLE 3

Evaluation of the activity on CNS of (±) racemic dropropizine, (+) dextrorotatory isomer and (−) laevorotatory isomer

| | Dose mg/kg p.o. | Duration of the sleeping time induced by barbiturates (mean ± SE; minutes) | Time spent in the sleeping condition (mean ± SE; seconds) |
|---|---|---|---|
| Controls | — | 22.58 ± 1.14 | 4.86 ± 0.60 |
| (±) | 25 | | |
| | 50 | 118.83 ± 25.69** | |
| | 100 | 132.33 ± 13.16** | |
| | 200 | 134.16 ± 17.55** | |
| (+) | 25 | | 6.18 ± 0.72 |
| | 50 | | 12.36 ± 0.9* |
| | 100 | | 28.92 ± 1.7* |
| | 200 | | |
| (−) | 25 | | 5.8 ± 0.84 |
| | 50 | 29.5 ± 2.59 | 5.7 ± 0.48 |

TABLE 3-continued

Evaluation of the activity on CNS of (±) racemic dropropizine, (+) dextrorotatory isomer and (−) laevorotatory isomer

| Dose mg/kg p.o. | Duration of the sleeping time induced by barbiturates (mean ± SE; minutes) | Time spent in the sleeping condition (mean ± SE; seconds) |
|---|---|---|
| 100 | 54.4 ± 7.36* | 13.68 ± 1.80 |
| 200 | 128.83 ± 17.14** | |

*P > 0.05 vs control
**P > 0.005 vs control
SE = Standard error.

TABLE 4

Acute toxicity (at 14 days from the administration) of (±) racemic dropropizine (+) dextrorotatory isomer and (−) laevorotatory isomer

| | Species | Administration route | $DL_{50}$ mg/kg (C.L. 95%) |
|---|---|---|---|
| (±) | mouse | p.o. | 900.2 (810.9–999.3) |
| | | i.p. | 339.7 (311.3–370.7) |
| | rat | p.o. | 606.9 (484.4–260.4) |
| | | i.p. | 392.9 (346.4–445.7) |
| (+) | mouse | p.o. | 871.7 (745.8–1021.6) |
| | | i.p. | 319.2 (263.4–587.5) |
| | rat | p.o. | 721.3 (594.7–802.1) |
| | | i.p. | 363.4 (291.6–473.2) |
| (−) | mouse | p.o. | 1287.2(1066.5–1553.4) |
| | | i.p. | 408.0 (320.4–519.5) |
| | rat | p.o. | 886.6 (692.7–1134.7) |
| | | i.p. | 401.3 (319.1–504.7) |

C.L. = Confidence limits.

From the results obtained the almost complete lack of activity on the Central Nervous System of the laevorotatory isomer, even though with unchanged antitussive and antiinflammatory activity, appears surprising.

The dextrorotatory isomer, on the other hand, for its activity on the Central Nervous System, can be used as mild sedative in elderly patients affected by hypereccitability of neurovegetative nature.

The following Examples further illustrate the invention without anyway limiting the scope thereof.

EXAMPLE 1

Preparation of (+)-dropropizine according to Method A (a) (−)-Methyl-o-isopropylidene-L-glycerate 30 Grams of NaNO₂ were added, in small portions and under stirring, to a solution of 52.5 g of (−)-L-serine in 3 l of H₂O and 75 ml of conc. HCl, cooled to 0° C. Stirring was continued for 24 hours keeping the temperature to 0° C., thereafter 10 g of $NaNO_2$ were added again, and stirring was continued for 16 hours at room temperature. Water was evaporated under reduced pressure.

150 Ml of $CH_3OH$, 15 ml of conc. HCl and 400 ml of 2,2-dimethoxypropane were added to the residue and the mixture was left under stirring for 2 hours at room temperature.

The so obtained ester was directly transformed in to the corresponding ketal, without recovering, according to the following procedure: after removing by filtration the formed solid, the filtrate was evaporated under vacuum and 400 ml of acetone, 100 ml of 2,2-dimethoxypropane, and 0.5 g of p-toluensulphonic acid were added to the residue and the mixture was left under stirring for 8 hours at room temperature. The formed solid was filtered off, the solvent was evaporated and the residual oil was distilled.

46 Grams of (−)-methyl o-isopropylidene-L-glycerate boiling at 77°–80° C./10 mmHg were obtained.

Yield: 57%; $[\alpha]_D^{22} -10.1°$ (pure).

Alternatively, the ketal can be obtained by the following method:

12.5 g of $ZnCl_2$ in 75 ml of acetone were stirred for 30′. 6 Grams of the methyl ester were added to the solution and the mixture was stirred for 2 hours. 25 Ml of $CHCl_3$ and 25 ml of a NaCl saturated aqueous solution were added thereto. The layers were separated and extracted several times with $CHCl_3$. The mixture was dried and the solvent evaporated. 3.52 Grams of an oil which is distilled under vacuo (see above) were obtained.

(b) (−)-2,3-o-Isopropylidene-sn-glycerol

A solution of 20 g of methyl-o-isopropylidene-L-glycerate in 100 ml of anhydrous ether was added to a suspension of 4 g of $LiAlH_4$ in 75 ml of anhydrous ether, adjusting the addition rate so as to keep a mild boiling. When the addition was over, the mixture was refluxed for half an hour.

The excess of $LiAlH_4$ was destroyed with an ethylacetate/ether mixture and a mixture $H_2O$/ethanol was subsequently added to make granular the previously formed jelly precipitate. After filtration, washing with ether, drying on $MgSO_4$, the solvent was evaporated and the residue distilled. 13.2 Grams of (−)-2,3-o-isopropylidene-sn-glycerol, boiling at 75°–76° C./10 mmHg, were obtained.

Yield 80%; $[\alpha]_D^{22} -13.2°$ (pure).

(c) (−)-2,3-o-Isopropylidene-sn-glycerol tosylate

A solution of 11.43 g of TsCl in pyridine was added to a solution of 6 g of the product obtained in (b) in anhydrous, ice-cooled pyridine. The molar ratio was 1:1. The mixture was left in ice-bath for 1 hour, then at room temperature for about 15 hours and then $H_2O+HCl$ were poured thereinto.

The mixture was extracted with $CHCl_3$, dried on $Na_2SO_4$ and the solvent was evaporated. 11 Grams of product were obtained which was used as such in following step.

(d) (+)-Glycerol-1-tosylate

The product (c) was dissolved in acetone and the mixture was heated to about 60° C. in the presence of 1N HCl for 1 hour. The acetone was evaporated and the residue was extracted with $CHCl_3$.

(e) (+)-Dropropizine

6 Grams of (+)-glycerol-1-tosylate and 8.475 g of N-phenyl-piperazine (molar ratio 1:2) in benzene were refluxed overnight. The formed precipitate was filtered and the filtrate evaporated.

3.5 Grams of product which was purified by a silica gel column chromatography, eluent $CHCl_3/CH_3OH$ 8:2, were obtained.

The so obtained product was crystallized from acetone.

M.p.: 104°–105° C.; $[\alpha]_D^{22} +9.7°$ (ethanol).

EXAMPLE 2

Preparation of (−)-dropropizine according to Method B

(a) 1,2,5,6-Diisopropylidene-D-mannitole

A mixture of $ZnCl_2$ (250 g) and 1.5 l of acetone was stirred for 30′. D-Mannitole (182 g, 1 mole) was added to the solution and stirring was continued for 2 hours. As main product, the 1,2,5,6-diisopropylidene-D-mannitole is produced together with small amounts of 1,2,3,4,5,6-triisopropylidene-D-mannitole and of 1,2-isopropylidene-D-mannitole.

The reaction mixture was treated with a NaCl saturated solution (500 ml) and extracted with 2×500 ml of $CHCl_3$ (higher phase).

The collected extracts were shaken with 1 liter of ammonium hydroxide (5%) to complex possible traces of $ZnCl_2$. The extracts were then dried on $Na_2SO_4$ and the solvent was evaporated.

The white solid residue was constituted almost exclusively by 1,2,5,6-diisopropylidene-D-mannitole. The triisopropylidene derivative was present in percentages from 5 to 10% (by weight) while monoisopropylidene derivative remained in the aqueous phase.

(b) (+)-1,2-Isopropylidene-sn-glycerol

The raw product of the previous step was dissolved in methanol and added dropwise to a sodium metaperiodate solution (160 g, 0.75 moles) in 1.5 l of $H_2O$, whose pH had been previously adjusted to 6 by addition of 2 g of LiOH. It is very important to check accurately the pH of the solution to avoid racemization occurs. The addition rate had to be adjusted so as the temperature did not exceed 35° C. The reaction was complete after 10 minutes. MeOH (1.3 l) was added and the pH was brought to 8 by addition of 5M KOH. The mixture was cooled to 10° C. and filtered under vacuum to remove the precipitate of $NaIO_3$ and $NaIO_4$.

$NaBH_4$ (25 g, 0.66 moles) was added to the filtrate. The reduction of the aldehyde was completed in 15 minutes.

The reaction mixture was first extracted with hexane (500 ml) to remove triisopropylidene-D-mannitole and then with $CHCl_3$ (1 liter) taking care of salting water with 170 g of NaCl. The extraction with $CHCl_3$ (500 ml) was repeated and the extracts were dried on $Na_2SO_4$. The residue was distilled after solvent evaporation. The product boils at 77°–78° C./10 mmHg; $[\alpha]_D^{20} +15.2°$ (EtOH, C=1%).

The yield was 45% calculated on D-mannitole (117 g of 1,2-isopropylidene-sn-glycerol, which can be stored at 5° C. for several months, without remarkable loss of optical activity, in the presence of 1 g of solid KOH each 200 g of product.

(c) (+)-1,2-Isopropylidene-sn-glycerol tosylate

A solution of p-toluensulphonyl chloride (12.95 g) in pyridine (15 ml) was added dropwise to a solution of (+)-1,2-isopropylidene-sn-glycerol (6.8 g) in pyridine (10 ml) cooled at 0° C. The mixture was left under stirring for ~18 hours at 0° C. and then poured into $H_2O$ to dissolve the formed salt. The product was extracted with $CHCl_3$. The extract was washed with diluted HCl to slight acidity, then with $NaHCO_3$ and, finally, with $H_2O$. The extract was dried on $Na_2SO_4$ and the solvent evaporated.

(d) (−)-Glycerol-1-tosylate

The raw product from the previous step was dissolved in acetone and hydrolized at 60° C. with 20 ml of 1N HCl for 1 hour. The acetone was evaporated and extracted with $CHCl_3$ possibly in a continuous way. The extracts were dried and after solvent evaporation, the product so obtained was crystallized from ether, m.p. 60°–61° C.; $[\alpha]_D^{20} -10°$ (EtOH, C=1%).

(e) (−)-Dropropizine

The product from the previous step and a double amount of phenylpiperazine in benzene were left to reflux for about 18 hours. The formed precipitate was filtered and washed thoroughly with EtOH. The filtrate was dried and granulated with ether. The white solid which formed was filtered and crystallized at least twice with acetone, m.p. 98°–100° C.; $[\alpha]_D^{25} -10°$ (EtOH, C=1%).

EXAMPLE 3

Pharmaceutical Compositions of Dropropizine Isomers

The pharmaceutical compositions and the active principle dosages hereinbelow reported are valid for both the dropropizine enantiomers, with antitussive prescription for the laevorotatory isomer and mild sedative prescription for the dextrorotatory isomer.

By way of example, the formulations with only one of the isomers are reported.

|  | Formulae | | |
|---|---|---|---|
|  | A | B | C |
| (a) SYRUP 100 ml of syrup contain: | | | |
| Laevorotatory isomer of dropropizine | g 0.100 | g 0.200 | g 0.300 |
| Saccharose | g 40.0 | g 40.0 | g 40.0 |
| Methyl-p-hydroxybenzoate | g 0.2 | g 0.2 | g 0.2 |
| Balsamic aroma | g 0.2 | g 0.2 | g 0.2 |
| Distilled $H_2O$ q.s. to | ml 100 | ml 100 | ml 100 |
| (b) ELIXIR 100 ml of elixir contain: | | | |
| Laevorotatory isomer of dropropizine | g 0.1 | g 0.2 | g 0.3 |
| Saccharose | g 40.0 | g 40.0 | g 40.0 |
| Ethanol | g 10.0 | g 10.0 | g 10.0 |
| Balsamic compound extr. | g 10.0 | g 10.0 | g 10.0 |
| Methyl-p-hydroxybenzoate | g 0.1 | g 0.1 | g 0.1 |
| Distilled $H_2O$ q.s. to | ml 100 | ml 100 | ml 100 |

| (c) DROPS | | |
|---|---|---|
|  | Pediatric use | Adult use |
| Laevorotatory isomer of dropropizine | g 1.000 | g 3.000 |
| Glycerine | g 20.000 | g 30.000 |
| Ethanol | g 10.000 | g 10.000 |
| Sodium saccharinate | g 0.500 | g 0.800 |
| Distilled $H_2O$ q.s. to | ml 100 | ml 100 |

We claim:

1. A pharmaceutical composition having antitussive activity comprising an effective amount of the 1-isomer of 3-(4-phenyl-1-piperazinyl)-1,2-propanediol isolated from a racemic mixture of the 1- and d-isomers, together with a pharmaceutically acceptable carrier, said composition exhibiting, when administered to a patient, an essentially equivalent antitussive activity but a substantially lower secondary sedative activity, than a composition comprising a like amount of the racemic mixture.

2. A method of treating coughs while minimizing undesirable central nervous system side effects which comprises orally administering to a patient an effective dosage of the pharmaceutical composition according to claim 1.

* * * * *